United States Patent [19]

Jackson

[11] 4,305,391

[45] Dec. 15, 1981

[54] DOUBLE WRAPPED TAMPON

[75] Inventor: David M. Jackson, Appleton, Wis.

[73] Assignee: Kimberly-Clark Corporation, Neenah, Wis.

[21] Appl. No.: 126,413

[22] Filed: Mar. 3, 1980

[51] Int. Cl.³ .............................................. A61F 13/20
[52] U.S. Cl. .................................... 128/270; 128/285; 128/287
[58] Field of Search ........................ 128/270, 285, 287

[56] References Cited

U.S. PATENT DOCUMENTS

| | | | |
|---|---|---|---|
| 3,683,912 | 8/1972 | Olson et al. ........................ | 128/285 |
| 3,999,549 | 12/1976 | Poncy et al. ........................ | 128/285 |
| 4,041,948 | 8/1977 | Flam et al. ........................ | 128/285 |
| 4,056,103 | 11/1977 | Kaczmarzyk et al. ............. | 128/285 |
| 4,100,324 | 7/1978 | Anderson et al. .................. | 428/288 |

*Primary Examiner*—William J. Van Balen
*Attorney, Agent, or Firm*—Howard Olevsky; William D. Herrick

[57] ABSTRACT

A tampon having an absorbent core with two fluid permeable wraps is provided. The combination of two wrapping layers aids in withdrawal particularly when a superabsorbent material is used as part of the absorbent and also may aid in the prevention of reverse fluid flow from the saturated tampon.

9 Claims, No Drawings

DOUBLE WRAPPED TAMPON

FIELD OF THE INVENTION

This invention relates to a tampon and particularly a tampon containing an outer wrap.

BACKGROUND OF THE INVENTION

Recently, tampons have been manufactured in such a way that an outer wrap is placed around an absorbent core. Wrappers have been utilized for a variety of purposes; among them, prevention of sloughing of individual fibers from the absorbent core during use, an insertion aid to provide a surface of lessened friction and a withdrawal aid. In the latter case, when superabsorbent material is present in the absorbent core of the tampon, a negative or suction pressure is developed along the surface of the tampon which tends to make the vaginal walls adhere to the outer surface and makes withdrawal uncomfortable.

Superabsorbent material has been considered particularly beneficial as an absorbent component in tampons because of its high absorbency per unit weight but the negative pressure developed by these materials has led to a series of attempts to provide an interfering or so-called "buffer" layer between superabsorbent material and the vagina. One such attempt is described in U.S. Pat. No. 3,999,549 in which a hydrophilic foam sheath surrounding a highly absorbent core is utilized to isolate the superabsorbent from the vagina. A similar concept by the same inventors is described in U.S. Pat. No. 4,020,841 with a subsidiary benefit set forth in both of these patents being the isolation of the absorbent material from vaginal contractions which would serve to prevent reverse fluid flow.

U.S. Pat. No. 3,683,912 discloses an absorbent tampon having an outer wrap of polypropylene fibers which is designed to reduce resistance to insertion.

Another patent concerned with difficulties inherent in the utilization of superabsorbent material as part of the absorptive component is U.S. Pat. No. 4,056,103. The tampon described therein embodies a wrapper which is a fluid permeable web with some measure of fluid retention capacity. The idea behind this invention is to ease withdrawal by providing a lubricated outer wrap obtained by fluid retention.

While the attempts to utilize an outer wrap to minimize the negative pressure encountered by the use of superabsorbent have been successful to some extent, the degree of success usually is accompanied by a concomitant decrease in the absorptive capabilities of the tampon. Absorptive capabilities in this context refer either to the rate of absorption, the outer wrap providing a barrier to some extent to the fluid uptake and/or to the amount of fluid absorbed. By their nature, tampons are restricted as to size and configuration and outer wraps or foam layers on the outside as described in U.S. Pat. No. 3,999,549 must replace needed absorptive volume with nonabsorptive or less absorptive volume in regard to the overall tampon construction. Also, while U.S. Pat. No. 3,999,549 describes the use of a foam outer layer to minimize the effect of vaginal contractions on the tampon, the foam layer itself would not be particularly advantageous to prevent reverse flow because the contractions would act to squeeze whatever menstrual exudate is within the interstices of the foam much like squeezing a sponge.

This invention provides a tampon which, not only is readily removable when a superabsorbent is used as part of the tampon absorbent material but this ease of removal can be retained without any noticeable decrease in absorption. In addition, reverse fluid flow, it is theorized, is substantially reduced when a tampon is made according to the teachings of this invention.

SUMMARY OF THE INVENTION

According to this invention, a tampon having an absorbent core material, a first fluid pervious wrap and a second fluid pervious wrap along with a withdrawal means is provided. The utilization of this double wrap accomplishes not only the advantages discussed in the preceding paragraph, but also allows the manipulation of absorptive flow and quantity characteristics as well as withdrawal and size configurations with substantially greater latitude than heretofore achieved. For example, a tampon can be made containing a substantially greater amount of superabsorbent material than previously contemplated and the increased absorbency resulting can be balanced against reduced bulk and, depending upon the particular characteristics of both the inner wrap and the outer wrap, ease of withdrawal.

It will be readily apparent to those in the art that various combinations of wraps can be used to accomplish a variety of modifying effects and, as a result, the choice and configuration of absorbent material and of the tampon in its entirety can be substantially expanded. Generally, however, with a tampon containing superabsorbent material as part of the absorbent matrix it is preferred that the outer and inner wrap have different characteristics relative to each other. For example, it is preferred that the inner wrap be partially fluid absorbent. This not only aids in minimizing withdrawal forces but also tends to aid in the prevention of reverse flow because it provides an additional absorptive capacity as well as the additional interface automatically present with the use of two wraps. The outer wrap, in comparison is preferably of a lower loft and basis weight than the inner wrap when superabsorbent is employed. The general concept of the particular relationship is to pass fluid through the outer wrap, rapidly. This is facilitated by making the pore size of the outer wrap substantially greater than the inner wrap. Once the fluid has rapidly passed through the first wrap it is then partially absorbed and more slowly passes through the second wrap. This controlled migration also acts to restrict the negative pressure resulting from the use of superabsorbents and will therefore aid in withdrawal.

In this context, suitable inner wrap material can be meltblown polyolefins, meltblown polyolefin-pulp mixtures and polyesters. Particularly preferred is meltblown polyolefin-pulp mixtures such as those described in U.S. Pat. No. 4,100,324. This nonwoven material has a fabric-like finish and is made up of an airformed matrix of thermal plastic polymeric fibers having an average fiber diameter of less than 10 microns and a multiplicity of individualized wood fibers dispersed throughout the matrix serving to space the microfibers from each other. This material is formed initially by utilizing a primary airstream with meltblown microfibers in a secondary airstream containing wood pulp fibers. The two are merged under turbulent conditions and placed upon a forming surface in an integrated airstream. If this material is chosen it may be necessary and/or desirable to increase the hydrophilicity of it by the use of suitable surfactants, the choice being determined by the amount of added hydrophilicity desired. In addition, with the choice of suitable wetting agents or surfactants the material can be rendered substantially more absorbent and due to the other variables discussed above for determining an ideal system under specific goals this may also be desirable.

Suitable outer wrap materials are spunbonded polyolefins, polyesters and the like. An example of a particularly preferred material is the polypropylene material described in U.S. Pat. No. 3,683,912. This outer wrap may also be treated with a wetting agent and/or surfactant and/or emollient material as desired again bearing in mind the control of the other variables and the ultimate goal of the performance of the tampon according to this invention.

One of the advantages in utilizing the particularly preferred inner and outer wrap in combination is that when the meltblown polypropylene wood fiber mixture is produced it can be directly layed on the polypropylene fibers of the outer wrap. When this laying step is complete, since the material which forms the inner wrap is heated there will be localized fusing in random contact areas between the two layers of material. This will be sufficient to bond the material and the subsequent wrapping of the tampon can be completed treating the inner and outer wrap as one material and thereby necessitating only one wrapping step. In addition, because both the inner and outer wrap are fusible, sealing of the wrap around the tampon can be accomplished by heat or, alternatively, ultrasonic means. The use of fusing as a means for adding the outer wrap is preferred because there will be no resultant interference with absorbency by the presence of adhesive on the wraps.

As discussed above, the outer and inner wrap combination is particularly beneficial when a superabsorbent is used as part of the absorbent material. Of course, there are benefits inherent in the double wrap concept without the superabsorbent as part of the absorbent component and, consequently, the scope of this invention is not limited to the presence of a superabsorbent or to any particular tampon configuration.

To illustrate the effect of the double wrap, several users were each given representative tampons which included first, a commercially available tampon sold under the KOTEX Heavy Duty trademark. This tampon has a spunbonded polypropylene outer cover which has not been treated by any chemical modifiers. It also contains a superabsorbent. For comparison, two tampons made according to this invention were given to an equal number of consumers. In one group a meltblown fiber combination of wood pulp and polypropylene having a basis weight of 25 gm/yd$^2$ was used as an inner wrap. In a second group the same inner wrap was used except that a basis weight of 40 gm/yd$^2$ was used. All tampons were made to weight 4.2 grams and therefore, the tampon having an inner wrap had less absorbent in the core in order to maintain the weight at a standard level.

A forced failure test was run initially in order to determine the average number of hours that the tampon would be used before failure occurred. The results were as follows:

| Sample | Hours |
|---|---|
| 25 gm/yd$^2$ | 5.8 ± 0.6 |
| 40 gm/yd$^2$ | 6.1 ± 0.5 |
| Commercial Tampon | 5.9 ± 0.6 |

The ± in this context, statistically means that 95% of the data fell within the parameters set forth, i.e. a 95% confidence level.

Comparison of overall grams absorbed indicates the following to a 95% confidence level:

| Sample | Grams Absorbed |
|---|---|
| 25 gm/yd$^2$ | 9.7 ± 1.4 |
| 40 gm/yd$^2$ | 10.3 ± 1.3 |
| Commercial Tampon | 10.9 ± 1.3 |

It is believed upon examination of this data that these results were not significantly different at the 95% confidence level for the differences noted. Although it should be noted that the tampon with the higher basis weight inner wrap performed better than the tampon with the lower basis weight inner wrap although again, it should be stressed that there is no significant absorptive difference even though there was less absorbent material present in the tampons which are the subject of this invention. Further evaluation relating to ease of removal indicated that removal discomfort was significantly and demonstrably eased when the inner wrap was used. For example, when over 300 tampons per type were tested by a variety of women, 14.51% of the tampons tested of the commercial tampon produced removal difficulty while 3.44% of the tampons of the lower basis weight wrap demonstrated removal difficulty and 6.43% of the tampons with the 40 gm/yd$^2$ basis weight demonstrated removal difficulty. When the tampons were each evaluated by 85 women, 29 had some difficulty with removal with the commercially available tampon, 9 with the lower basis weight inner wrapped tampon and 18 with the higher basis weight inner wrapped tampon.

It is apparent, therefore, that substantial advantages in removal without loss in absorptive protective performance (protective meaning hours of protection) and possible substantial advantages in preventing reverse flow can be obtained according to the teachings of this invention.

What is claimed is:
1. A tampon comprising in combination:
   (a) an absorbent matrix;
   (b) withdrawal means;
   (c) a fluid pervious outer wrap selected from the group consisting of polyolefins and polyesters; and,
   (d) a fluid pervious inner wrap selected from the group consisting of meltblown polyolefins, meltblown polyolefin/pulp mixtures and polyesters, the outer wrap having a lower loft and basis weight than the inner wrap.

2. The tampon according to claim 1 in which the inner and outer wrap are bonded together.

3. The tampon according to claim 1 wherein the inner wrap is treated with a wetting agent.

4. The tampon according to claim 1 wherein the outer wrap is treated with a wetting agent.

5. The tampon according to claim 1 wherein the outer and inner wraps are treated with a wetting agent.

6. The tampon according to claim 1 wherein the absorbent matrix includes superabsorbent.

7. The tampon according to claim 1 wherein the outer wrap is treated with an emollient.

8. The tampon according to claim 1 in which the outer wrap is treated with an emollient and the inner wrap is treated with a wetting agent.

9. The tampon according to claims 1, 2, 3, 4, 5, 6, 7 or 8 in which the inner and outer wraps are locally fused.

* * * * *